US012616414B2

(12) United States Patent
Weiss et al.

(10) Patent No.: US 12,616,414 B2
(45) Date of Patent: May 5, 2026

(54) SMART CARDIAC ELECTROPHYSIOLOGICAL (EP) MAP

(71) Applicant: BIOSENSE WEBSTER (ISRAEL) LTD., Yokneam (IL)

(72) Inventors: Shaked Weiss, Kiryat Ata (IL); Jonathan Yarnitsky, Haifa (IL); Ben Ami Novogrodsky, Haifa (IL); Meytal Segev, Haifa (IL); Itay Ostrov, Kfar Yehezkel (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 460 days.

(21) Appl. No.: 18/107,751

(22) Filed: Feb. 9, 2023

(65) Prior Publication Data

US 2023/0277112 A1     Sep. 7, 2023

Related U.S. Application Data

(60) Provisional application No. 63/317,117, filed on Mar. 7, 2022.

(51) Int. Cl.
| | |
|---|---|
| *A61B 5/367* | (2021.01) |
| *A61B 5/00* | (2006.01) |
| *A61B 5/287* | (2021.01) |
| *A61B 5/339* | (2021.01) |

(52) U.S. Cl.
CPC .............. *A61B 5/367* (2021.01); *A61B 5/287* (2021.01); *A61B 5/339* (2021.01); *A61B 5/6852* (2013.01); *A61B 5/7221* (2013.01); *A61B 5/7475* (2013.01)

(58) Field of Classification Search
CPC ................................ A61B 5/367; A61B 5/339
USPC .......................................................... 600/523
See application file for complete search history.

(56) References Cited

U.S. PATENT DOCUMENTS

| | | | |
|---|---|---|---|
| 8,456,182 B2 | 6/2013 | Bar-Tal | |
| 9,050,011 B2 | 6/2015 | Rubinstein et al. | |
| 10,172,536 B2 | 1/2019 | Maskara | |
| 10,376,221 B2 | 8/2019 | Iyun | |
| 10,555,680 B2 | 2/2020 | Thakur | |
| 2009/0099468 A1 | 4/2009 | Thiagalingam et al. | |
| 2019/0332729 A1* | 10/2019 | Villongco | .............. G06F 30/20 |
| 2021/0386355 A1 | 12/2021 | Ravuna et al. | |
| 2022/0225925 A1* | 7/2022 | Cohen | .................... A61B 34/20 |

FOREIGN PATENT DOCUMENTS

| | | |
|---|---|---|
| EP | 2501280 B1 | 10/2018 |
| WO | WO2019217430 A1 | 11/2019 |

\* cited by examiner

*Primary Examiner* — Nicole F Johnson

(57) ABSTRACT

A system for generating an electrophysiological (EP) map includes a display and a processor. The processor is configured to (i) receive multiple EP data points comprising respective locations and EP values, generated from signals acquired by one or more electrodes of a catheter that are in contact with tissue of a cardiac chamber, (ii) score the received data points with respective quality scores, (iii) for a given unit volume of the EP map, select, from among the data points whose locations fall in the unit volume, a data point with a highest quality score, for use in generating the EP map, and (iv) visualize the EP map to a user, on the display.

10 Claims, 3 Drawing Sheets

SMART CARDIAC ELECTROPHYSIOLOGICAL (EP) MAP

CROSS-REFERENCE TO RELATED APPLICATION

This application claims the benefit of U.S. Provisional Patent Application 63/317,117, filed Mar. 7, 2022, which is incorporated herein by reference.

FIELD OF THE DISCLOSURE

The present disclosure relates generally to cardiac electrophysiological (EP) mapping, and particularly to automation of generation of data points for cardiac EP maps.

BACKGROUND OF THE DISCLOSURE

Automatic processing of catheter-acquired EP signals was previously described in the patent literature. For example, U.S. Patent Application Publication 2009/0099468 describes a method, an apparatus, and a computer program product for automated processing of intracardiac electrophysiological data. The method comprises the steps of: recording electrogram data and corresponding spatial location data of an electrode recording the electrogram data, the recorded electrogram data comprising a plurality of beats; defining at least one reference channel containing a reference beat for determining temporal locations and against which beats of the recorded electrogram data are compared; examining the recorded electrogram data and defining a temporal location for each beat of the recorded electrogram data; creating an index of the temporal locations and other information of the beats within the recorded electrogram data; analyzing in real-time at least one electrophysiological feature of the recorded electrogram data suggestive of a physiological condition; and providing an updated index wherein the other information comprises results of the analysis.

As another example, U.S. Pat. No. 10,376,221 describes automatic creation of multiple electroanatomic maps. Cardiac electrograms are recorded in a plurality of channels. Beats are classified automatically into respective classifications according to a resemblance of the morphologic characteristics of the beats to members of a set of templates. Respective electroanatomic maps of the heart are generated from the classified beats.

The present disclosure will be more fully understood from the following detailed description of the examples thereof, taken together with the drawings in which:

DETAILED DESCRIPTION OF EXAMPLES

Overview

Figure 1:
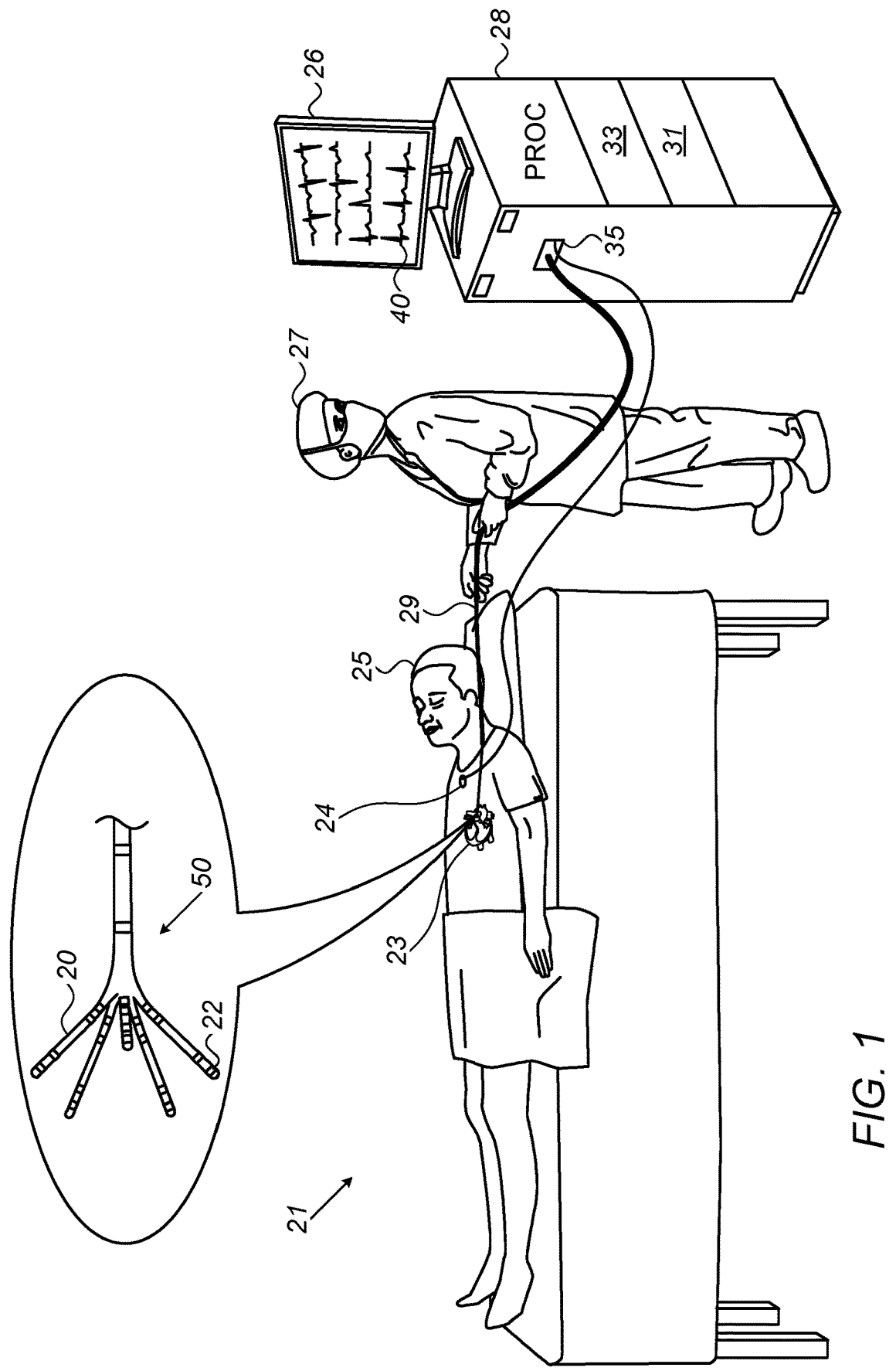
FIG. 1 is a schematic, pictorial illustration of a system for electrophysiological (EP) mapping and ablation, in accordance with an example of the present disclosure.

Probe-based (e.g., catheter-based) cardiac diagnostic and therapeutic systems may measure multiple intra-cardiac electrophysiological (EP) signals, such as electrograms (EGM), during an invasive procedure. Such systems acquire multiple intra-cardiac signals using one or more electrodes (e.g., multiple electrodes) that are fitted at the distal end of the probe. For example, to reduce the time required to EP map a heart chamber, e.g., to acquire EGM signals of the chamber, a catheter carrying a large number of electrodes (e.g., 256), such as a basket catheter, may be used. In many cases, the analysis of such a large number EP signals acquired in parallel is done, for example, to generate data points used to generate an EP map in continuous mode (automatically), in order to enable processing such a vast amount of EP information.

The generation of the data points typically involves applying rejection criteria (e.g., the use of "filtering" to avoid using "erroneous" data points, such as those that are irrelevant or too noisy) at any given time. The physician performing the procedure therefore needs to set "adequate" filtering criteria and to monitor the filtration process in order to ensure that its settings produce a sufficient quality (e.g., relevant, stable) of data points (e.g., for an EP map).

Thus, acquired data points are typically subjected to filtration (e.g., rejection criteria) to remove data points that may be incorrect (e.g., unstable) or irrelevant (e.g., acquired from the blood pool instead of the chamber surface). When acquired data points are subjected to multiple filters each having individual thresholds, a failure of a point to pass any one filter causes the point to be rejected, even if it might be acceptable if not high-quality, all things considered. For large total numbers of data points acquired during an EP mapping session, which, using modern multi-electrode mapping catheters, number in the tens of thousands, it is difficult for a physician to tell whether the filter setting levels are reasonable, e.g., whether too many or too few data points are being rejected. Furthermore, in conventional maps, once a data point is acquired, it becomes "permanent," with no ability to replace the data point with a higher quality point, thus preventing the map from reaching the highest potential quality achievable within the data capable of being acquired.

Examples of the present disclosure that are described herein provide algorithms and visualizations for a high level (e.g., based mainly on clinical input) and automated selection of data points to, for example, generate and update an EP map in real time. In some examples, each newly received data point is scored by a processor with a disclosed quality score. The disclosed algorithm (called SMARTMAP) prioritizes the scores of high-quality data points over lower-quality data points when constructing (e.g., visualizing) an EP map, by swapping data-point selections according to their quality score. To this end the processor is configured to replace a previously-selected data point within a given unit volume defined below with a newly-acquired data point in the given unit volume, in response to finding that the quality score of the newly-acquired data point is larger than the quality score of the previously-selected data point.

The aforementioned quality score of a data point, also called herein a "smart index," is an output of a weight function which considers several data point parameters obtained during a preprocessing stage (e.g., annotations) of an intra-cardiac waveform. The weighted parameters include, for example, cycle length, signal amplitude, stability of local activation time (LAT), electrode stability and level of contact touch with tissue during acquisition, among others, as described below. In some examples, the processor rates each new data point with a normalized quality score ranging between 0 and 1.

In some examples, the process of data point selection and EP map updating according to newly selected data points is done in real time while continuous acquisition is in progress. The disclosed SmartMap technique reduces physician work load (i.e., user workflow) by removing data point filtering steps, which results in simpler and faster data point acquisition and quick EP map settings. User involvement and decision making are therefore limited to high-level settings, such as arrhythmia type and quality-score threshold, all performed via a high-level GUI.

One example of high-level visualization provided comprises a layer of the EP map, sometimes referred to as a "heat map", that spatially indicates EP map quality according to the quality score (i.e., "smart index") of the graded data points. This layer graphically indicates regions of a cardiac chamber to guide the physician for mapping catheter insertion. Where the quantity of data points is too low (e.g., spatially sparse), the physician can collect additional data points so as to improve the EP map quality in such regions. Another high-level visualization is an adjustable scale for the aforementioned user-selected threshold value of the quality score, so the user can fine-tune the EP map quality by changing a quality scoring threshold below which candidate data points are not considered.

System Description

FIG. 1 is a schematic, pictorial illustration of a system 21 for electrophysiological (EP) mapping and ablation, in accordance with an example of the present disclosure. FIG. 1 depicts a physician 27 using an EP mapping catheter 29 to perform an EP mapping of a heart 23 of a patient 25. Catheter 29 comprises, at its distal end, a multi-channel electrode array 50 comprising one or more arms 20, each of which is coupled to mapping-electrodes 22. During the mapping procedure, electrodes 22 acquire and/or inject signals from and/or to the tissue of heart 23. In particular, electrodes 22 acquire intracardiac EP signals, such as unipolar and/or bipolar electrograms (e.g., electrograms 40 shown on a display 26 of system 21).

Catheter 29 may be further used to perform an ablation, such as radiofrequency (RF) or irreversible electroporation (IRE).

The respective locations of mapping-electrodes 22 inside heart 23 (i.e., where the electrograms are measured) are also tracked, such that a processor 28 may link each acquired electrogram with the location at which the signal was acquired to, for example, generate a data point for an EP map. System 21 externally senses electrical position signals using a plurality of external electrodes 24 coupled to the body of patient 25. For example, three external electrodes 24 may be coupled to the patient's chest, and another three external electrodes may be coupled to the patient's back. For ease of illustration, only one external electrode is shown in FIG. 1.

An example of a system capable of using the sensed electrical position signals to track the locations of mapping-electrodes 22 inside heart 23 of the patient is the CARTO® 3 system (produced by Biosense Webster, Irvine, California). The CARTO® 3 system uses a position tracking method named Advanced Current Location (ACL), which is described in detail in U.S. Pat. No. 8,456,182 whose disclosure is incorporated herein by reference.

A data acquisition module 33 receives the multiple electrogram conveyed to an electrical interface 35 over a wire link that runs in catheter 29. Processor 28 of system 21 receives these cardiac signals via an electrical interface 35, and, after processing these into data points, uses the disclosed algorithm to sort the data points based on, for example, different predefined arrhythmia types, e.g., atrial fibrillations, tachycardias, flutter, and others. In this way physician 27 doesn't need to operate a menu of data filters in order to determine the suitability of the acquired data points for use in an EP map. It is noted that the disclosed algorithms herein merely represent some exemplary algorithms among many that could be used within the scope of the appended claims.

Processor 28 stores the acquired data points in a memory 31 for further analysis, such as for constructing an EP map. An example of an EP map that processor 38 may produce from automatically sorted data points is a local activation time (LAT) map. A method for generating an LAT map is described in U.S. Pat. No. 9,050,011, which is assigned to the assignee of this application.

Processor 28 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 28 runs a dedicated algorithm that enables processor 28 to perform the steps described in FIG. 3.

The example illustration shown in FIG. 1 is chosen purely for the sake of conceptual clarity. Other types of multi-electrode sensing geometries, such as of the Lasso® catheter (produced by Biosense Webster) or a basket catheter, may also be employed. Additionally, contact sensors may be fitted at the distal end of electro-anatomical catheter 29 to transmit data indicative of the physical quality of electrode contact with tissue.

Method for Automatic Quality Scoring of Data Points

Figure 2:
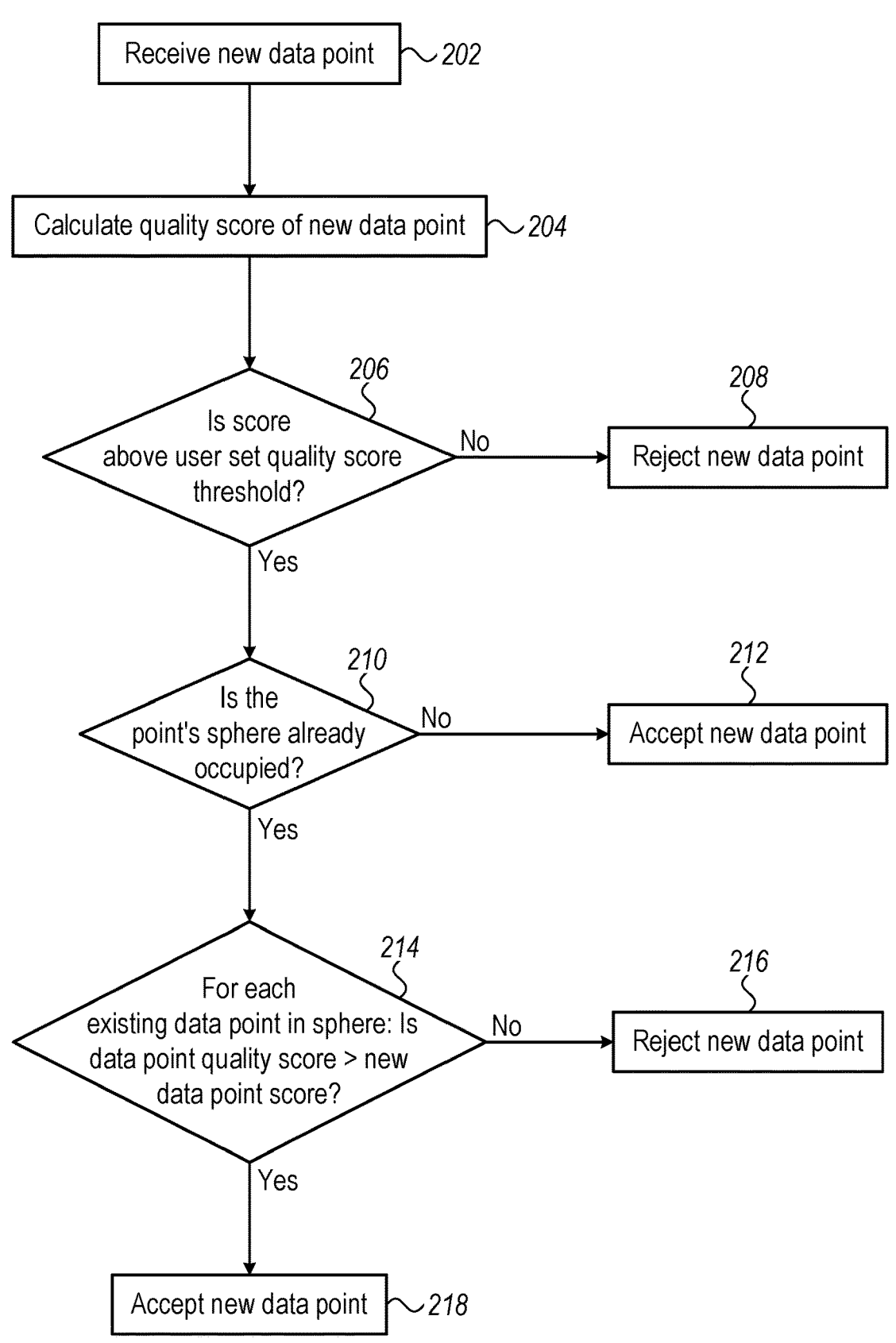
FIG. 2 is a flow chart that schematically illustrates a method for considering a candidate data point based on automatic quality scoring of the data point, in accordance with an example of the present disclosure.

FIG. 2 is a flow chart that schematically illustrates an example method for considering (i.e., rejecting or accepting) a candidate data point based on automatic quality scoring of the data point, in accordance with an example of the present disclosure. The algorithm, according to the presented example, carries out a process that begins with processor 28 receiving (e.g., uploading) a new data point, at a new data point receiving step 202. Received data points are aggregated by the processor (e.g., stored in memory 31) as part of a point cloud that may be used in generating an EP map or for other uses.

At quality score calculation step 204, processor 28 calculates the quality score of the data point, according to Eq. 1 below.

Then, processor 28 compares the calculated quality score to a user-set quality score threshold, at a comparison step 206. If the calculated quality score is lower than the threshold, processor 28 rejects the new data point, at data point rejection step 208.

If the calculated quality score is higher than the threshold, processor 28 checks if a unit volume of predefined size that encompass the newly received data point (e.g., a sphere of predefined radius such as 1 mm), is occupied by one or more existing data points, at data points existence checking step 210.

If the answer is no, meaning that the newly received data point is the only data point in the predefined unit volume, processor 28 accepts the data point, at data point accepting step 212.

If the answer is yes, processor 28 checks if the quality score of the newly received data point is higher than those of the existing data points in the unit volume, at a quality score value comparison step 314.

If the answer is no, processor 28 rejects the new data point, at data point rejection step 316. If the answer is yes, processor 28 accepts the data point, at data point accepting step 312. The accepted data point (from either step 212 or step 218) can be used by the processor to update an existing EP map.

Quality Score of Data Point in Smartmap

As noted above, the smart index is an outcome of a weight function which weighs several parameters of a data point, as listed, for example, in Table I below. Each candidate data point is rated with a normalized score (also called smart index) ranging between 0 and 1.

An exemplary equation of data point smart index is:

$$\frac{\sum_{n=1}^{N} \text{parameter's } weight_n * \text{parameter's } score_n}{\sum_{n=1}^{N} \text{parameter's } weight_n}, \quad \text{Eq. 1}$$

where N is the total number of parameters (see Table I of parameters below), with each parameter given a weight, e.g., a score from 1 to 5. Again, the parameter's normalized score is a number ranging between 0 and 1.

TABLE I

| Parameter Name | Parameter Weight | Parameter Score |
|---|---|---|
| Pattern matching | 5 | (−1) to 1 According to the PM correlation score |
| CL | 2 | $|\text{Current } CL - \text{median } CL| \equiv \Delta$ $\sigma^2 = CL$ variance $score = \begin{cases} 1 - \dfrac{\Delta}{\sigma^2}, & \text{current } CL \text{ is in range} \\ 0, & \text{current } CL \text{ is out range} \end{cases}$ |
| LAT stability | 3 | $|\text{Current } LAT - \text{Prev. beat } LAT| \equiv \Delta$ $score = \begin{cases} 1 - \dfrac{\Delta}{12}, & \Delta \le 12 \\ 0, & \Delta > 12 \end{cases}$ |
| Complex data point (e.g., LAM, CFAE) | 5 | 1/0 |
| TPI | 4 | 1 (touch) /0 (no touch or unknown) |
| Position stability | 3 | $|\text{Current position} - \text{Prev. beat position}| \equiv \Delta$ $score = \begin{cases} 1 - \dfrac{\Delta}{10}, & \Delta \le 10 \\ 0, & \Delta > 10 \end{cases}$ |
| Respiration | 5 | 1/0 (in/out respiration threshold) |

6

TABLE I-continued

| Parameter Name | Parameter Weight | Parameter Score |
|---|---|---|
| Location (CPM) | 2 | 0.2 |
| SNR | 2 | $score = \begin{cases} \dfrac{SNR}{10}, & SNR \le 10 \\ 1, & SNR > 10 \end{cases}$ |
| $\left|\dfrac{dV}{dt}\right|$ | 2 | $score = \begin{cases} \left|\dfrac{dV}{dt}\right| \Big/ 5, & \left|\dfrac{dV}{dt}\right| \le 5 \\ 1, & \left|\dfrac{dV}{dt}\right| > 5 \end{cases}$ |

In Table I, complex fractionated atrial electrograms (CFAE) and late activation mapping (LAM indicate complex EP signal behavior, such as those from a scarred tissue region. Because this deserves focus from the clinician, this distinction may therefore receive a high weight, at least for some arrhythmias.

In Table I, pattern matching is a test of data point consistency over cardiac cycles (a value of correlation between cardia cycles).

CL stands for cardia cycle length.

TPI stands for touch pressure index (or contact pressure index), which estimates contact force of a catheter electrode with a tissue wall during acquisition of the data point.

Position stability is a measure of electrode position consistency during acquisition over two or more cardiac cycles.

Respiratory weights adversely impact respiration on acquisition, such as introducing noise to signals.

Location CPM is a measure of the aforementioned ACL position tracking technique on electrode location consistency during acquisition.

SNR stands for the signal to noise ratio, which, if low, indicates a less robust acquisition.

$$\left|\frac{dV}{dt}\right|$$

reflects tor the sharpness of the signal deflections.

Table I is brought by way of example only. Other parameter lists may be different.

Graphical User Interface Tools for Smartmap

Figure 3:
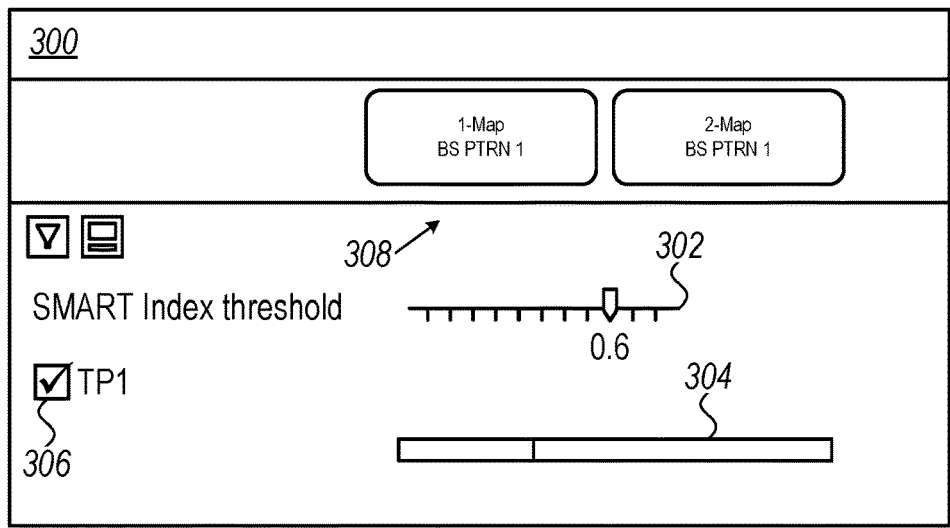
FIG. 3 is a schematic illustration of a graphical user interface (GUI) of the electrophysiological (EP) mapping system of FIG. 1, the GUI including a scale for setting a quality scoring threshold, in accordance with an example of the present disclosure.

FIG. 3 is a schematic illustration of a graphical user interface (GUI) 300 of electrophysiological (EP) mapping system 21 of FIG. 1, GUI 300 including a scale 302 for setting a quality scoring threshold, in accordance with an example of the present disclosure.

GUI 300 further includes a status bar 304 on the level of correlation results of pattern matching. A low value may mean sub-optimal acquisition conditions, which may indicate to a physician about a need to improve acquisition conditions in order to produce more meaningful EP data.

A TPI check box 306 allows a user to include a TPI weight, a time-consuming step in the process of accepting data points, e.g., for updating an EP map.

Finally, region 308 presents active EP maps, through which the user can toggle in order to, for example, adjust thresholds according to map type or arrhythmia type in question.

FIG. 3 is an example brought solely for the sake of describing an example. An actual GUI is typically far more elaborate, including, for example, numerous icons and graphics that are omitted herein for simplicity of presentation.

Figure 4:
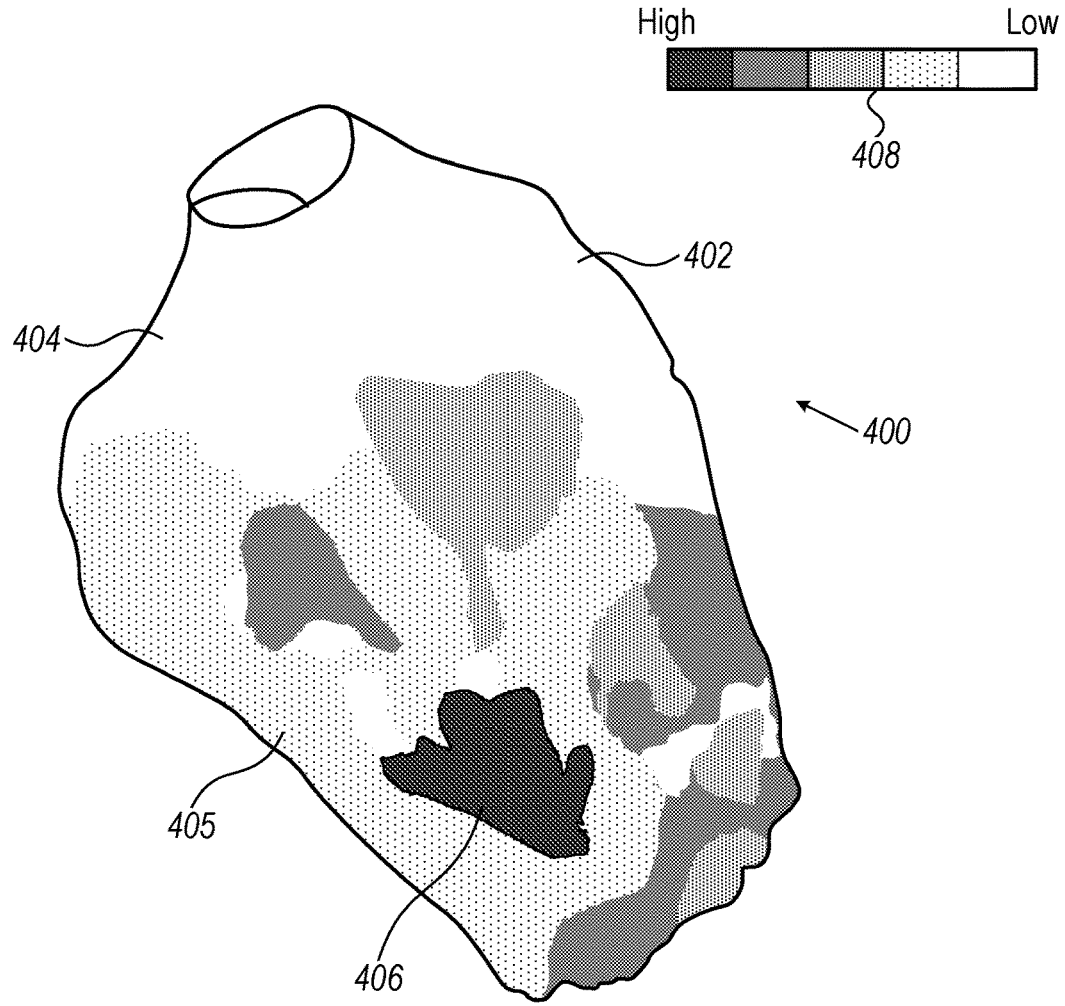
FIG. 4 is a schematic illustration of an informative layer of an EP map, the layer spatially indicating EP map quality according to quality score of the automatically accepted data points by the process of FIG. 2, in accordance with an example of the present disclosure.

FIG. 4 is a schematic illustration of an informative layer 400 of an EP map, layer 400 spatially indicating quality of the EP map according to quality score of the automatically accepted data points by the process of FIG. 2, in accordance with an example of the present disclosure. The shown map depicts anatomy 402 of a left ventricle being EP mapped with a catheter.

A scale 408 indicates to a user a quality score of data points at different regions of mapped anatomy 402. As seen, some regions (404) have not yet been mapped. Some regions (e.g., highlighted regions 405) are mapped at various medium quality score levels of data points. Finally, some regions, such as region 406, are mapped with high quality score data points. Using layer 400, which is a type of heat map of quality score of accepted and used data points, which a physician performing the EP mapping can use to direct the catheter to regions where EP map quality can be improved.

EXAMPLES

Example 1

A system (21) for generating an electrophysiological (EP) map includes a display (26) and a processor (28). The processor (28) is configured to (i) receive multiple EP data points comprising respective locations and EP values, generated from signals (40) acquired by one or more electrodes (22) of a catheter (29) that are in contact with tissue of a cardiac chamber, (ii) score the received data points with respective quality scores, (iii) for a given unit volume of the EP map, select, from among the data points whose locations fall in the unit volume, a data point with a highest quality score, for use in generating the EP map, and (iv) visualize the EP map to a user, on the display (26).

Example 2

The system according to example 1, wherein the processor (28) is configured to adjust the quality score according to a user-selected type of arrhythmia.

Example 3

The system according to any examples 1 and 2, wherein the quality score comprises a weighted scoring of at least two of (i) signal (40) pattern matching, (ii) annotated cycle length, (iii) LAT stability, (iv) complex/simple data point flagging, (v) electrode contact pressure index, (vi) electrode position stability (vii) respiratory flax, and (vii) signal SNR, and (viii) sharpness of signal deflection.

Example 4

The system according to any of examples 1 through 3, wherein the processor (28) is configured to replace a previously-selected data point of the given unit volume with a newly-acquired data point in the given unit volume, in response to finding that the quality score of the newly-acquired data point is larger than the quality score of the previously-selected data point.

Example 5

The system according to any of examples 1 through 4, wherein the processor (28) is further configured to generate and present to the user on the display (26) a layer of the EP map that spatially indicates a quality of the EP map according to a quality score of the received selected data points.

Example 6

The system according to any of examples 1 through 5, wherein the processor (28) is further configured to display a graphical user interface (GUI) that enables the user to set a threshold of the quality score, and to reject any data point whose quality score is below the threshold.

Example 7

A method for generating an electrophysiological (EP) map, the method including receiving multiple EP data points comprising respective locations and EP values, generated from signals (40) acquired by one or more electrodes (22) of a catheter (29) that are in contact with tissue of a cardiac chamber. The received data points are scored with respective quality scores. For a given unit volume of the EP map, a data point with a highest quality score is selected from among the data points whose locations fall in the unit volume, for use in generating the EP map. The EP map is visualized to a user, on a display (26).

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for generating an electrophysiological (EP) map, the system comprising:

a display;

a catheter having one or more electrodes, the one or more electrodes configured to contact cardiac tissue and acquire multiple EP data points within a cardiac chamber of a patient; and a processor, configured to:

receive the EP data points, each data point comprising a respective spatial location within the cardiac chamber and an EP value, generated from signals acquired by the one or more electrodes;

score the received data points with respective quality scores, each quality score being based on at least two data point parameters;

generate an EP map of at least a portion of the cardiac chamber, based on the acquired data points;

for each of a plurality of predefined unit volumes partitioning the EP map, select from among the data points whose locations fall within the respective unit volume, a data point having a highest quality score, wherein only the selected data point for each unit volume is used in generating the EP map;

replace, in any of the unit volumes, the selected data point if a newly-acquired data point within that unit volume has a higher quality score; and visualize the EP map to a user, on the display.

2. The system according to claim 1, wherein the processor is configured to adjust the quality score according to a user-selected type of arrhythmia.

3. The system according to claim 1, wherein the quality score comprises a weighted scoring of at least two data point parameters selected from: i) signal pattern matching, (ii) annotated cycle length, (iii) LAT stability, (iv) complex/simple data point flagging, (v) electrode contact pressure index, (vi) electrode position stability (vii) respiratory flax, (vii) signal SNR, and (viii) sharpness of signal deflection.

4. The system according to claim 1, wherein the processor is further configured to generate and present to the user on the display a layer of the EP map that spatially indicates a quality of the EP map according to a quality score of the selected data points.

5. The system according to claim 1, wherein the processor is further configured to display a graphical user interface (GUI) that enables the user to set a threshold of the quality score, and to reject any data point whose quality score is below the threshold.

6. A method for generating an electrophysiological (EP) map, the method comprising:

inserting a catheter into a cardiac chamber of a patient, the catheter having one or more electrodes, the one or more electrodes configured to contact cardiac tissue within the cardiac chamber;

acquiring, by the one or more electrode, multiple EP data points within the cardiac chamber, each data point comprising a respective spatial location within the cardiac chamber and an EP value, generated from signals acquired by the one or more electrodes;

scoring the received data points with respective quality scores, each quality score being based on at least two data point parameters;

generating an EP map of at least a portion of the cardiac chamber, based on the acquired data points;

for each of a plurality of predefined unit volumes partitioning the EP map, selecting from among the data points whose locations fall within the respective unit volume, a data point having a highest quality score, wherein only the selected data point for each unit volume is used in generating the EP map;

replacing, in any of the unit volumes, the selected data point if a newly-acquired data point within that unit volume has a higher quality score; and visualizing the EP map to a user, on a display.

7. The method according to claim 6, further comprising adjusting the quality score according to a user-selected type of arrhythmia.

8. The method according to claim 6, wherein the quality score comprises a weighted scoring of at least two data point parameters selected from (i) signal pattern matching, (ii) annotated cycle length, (iii) LAT stability, (iv) complex/simple data point flagging, (v) electrode contact pressure index, (vi) electrode position stability (vii) respiratory flax, (vii) signal SNR, and (viii) sharpness of signal deflection.

9. The method according to claim 6, further comprising generating and presenting to the user on the display a layer of the EP map that spatially indicates a quality of the EP map according to a quality score of the selected data points.

10. The method according to claim 6, further comprising displaying a graphical user interface (GUI) that enables the user to set a threshold of the quality score, and to reject any data point whose quality score is below the threshold.

\*    \*    \*    \*    \*